(12) United States Patent
Wilson

(10) Patent No.: US 7,815,688 B2
(45) Date of Patent: Oct. 19, 2010

(54) LAP JOINT FOR PROSTHETIC FOOT

(76) Inventor: Michael T. Wilson, 2711 Cartwright Rd., Missouri City, TX (US) 77459

(*) Notice: Subject to any disclaimer, the term of this patent is extended or adjusted under 35 U.S.C. 154(b) by 1019 days.

(21) Appl. No.: 11/379,298

(22) Filed: Apr. 19, 2006

(65) Prior Publication Data
US 2007/0250178 A1    Oct. 25, 2007

(51) Int. Cl.
A61F 2/68    (2006.01)
A43B 23/28    (2006.01)

(52) U.S. Cl. .......................................... 623/53; 36/58.6

(58) Field of Classification Search ............... 623/32, 623/49, 52, 53, 55; 602/28; 36/24.5, 58.6
See application file for complete search history.

(56) References Cited

U.S. PATENT DOCUMENTS

| | | | | |
|---|---|---|---|---|
| 1,424,264 A | * | 8/1922 | Shrodes | 623/52 |
| 1,911,816 A | * | 5/1933 | Dodge | 36/24.5 |
| 4,998,747 A | * | 3/1991 | Dimier et al. | 280/631 |
| 5,116,384 A | | 5/1992 | Wilson et al. | |
| 5,393,303 A | * | 2/1995 | Shiono | 602/27 |
| 5,443,527 A | | 8/1995 | Wilson | |
| 5,463,823 A | * | 11/1995 | Bell et al. | 36/11.5 |
| 5,482,513 A | | 1/1996 | Wilson | |
| 6,101,743 A | * | 8/2000 | Brown | 36/102 |
| 6,712,860 B2 | * | 3/2004 | Rubie et al. | 623/55 |
| 7,267,656 B2 | * | 9/2007 | Cooper | 602/27 |
| 2003/0009238 A1 | * | 1/2003 | Whayne | 623/32 |
| 2005/0033451 A1 | * | 2/2005 | Aigner et al. | 623/53 |
| 2005/0054963 A1 | * | 3/2005 | Ingimundarson | 602/27 |
| 2006/0079822 A1 | * | 4/2006 | Hjorth | 602/28 |
| 2007/0203585 A1 | * | 8/2007 | Wilson | 623/55 |

OTHER PUBLICATIONS

"Modular Prosthetic Feet—High-Performance Composite"; (1 p.), 2006 Ottobock Catalog.

* cited by examiner

Primary Examiner—Bruce E Snow
Assistant Examiner—Melissa Montano
(74) Attorney, Agent, or Firm—Conley Rose, P.C.

(57) ABSTRACT

Apparatus and methods for a prosthetic foot for attachment to a socket worn by an amputee. In an embodiment, the prosthetic foot comprises a body including a forefoot portion and a heel portion. In addition, the prosthetic foot comprises at least one attachment member extending from the body and conformable to the socket.

18 Claims, 8 Drawing Sheets

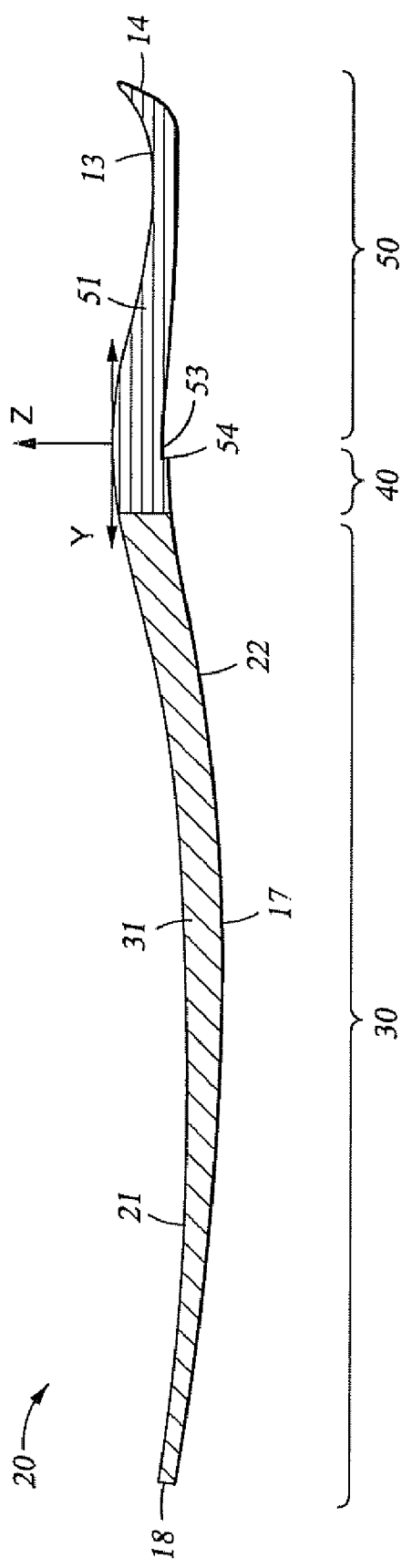
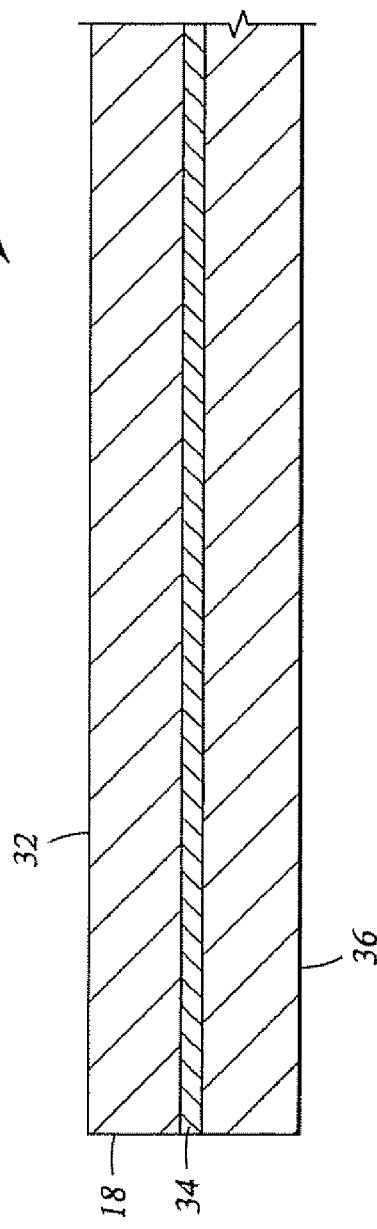
Fig. 4
Fig. 5

LAP JOINT FOR PROSTHETIC FOOT

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND

1. Field of the Invention

The present invention relates generally to a prosthetic foot. More particularly, the present invention relates to a prosthetic foot including a lap joint.

2. Background of the Invention

A useful prosthetic foot should simulate the operation and motion of an anatomical foot. An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement of the ball of the foot upward and downward, respectively, with respect to the heel. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

In addition, it is desirable for a prosthetic foot to provide a spring effect during use (e.g., be capable of absorbing, storing, and releasing energy). At a minimum, the prosthesis should store enough energy to return itself to a relaxed, unflexed position when external forces are removed. Such a spring effect may be accomplished by the inclusion of energy-storing components such as coil springs. However, such energy-storing components may significantly increase the bulk and weight of the prosthesis, which may not be suitable for some amputees. For instance, additional weight and/or bulk may result in a prosthesis that is too heavy for some patients, such as geriatric patients, very young patients, or other patients who suffer some degree of muscular weakness.

Further, a useful prosthesis should provide a secure and reliable means for attaching the prosthesis to the amputee. Failure of the connection between the prosthesis and the amputee may result in injury to the amputee and may also necessitate expensive repairs or potentially a complete replacement of the prosthesis. It is also desirable to provide methods for connecting the prosthesis to the amputee that do not significantly inhibit the ability of the prosthetic foot to simulate the motion and flexion of the anatomical foot.

In some cases, the foot may be only partially amputated. In the US, the common reasons for partial (forefoot) amputations are: peripheral vascular disease, congenital deformities, trauma, infection, and tumors. There are at least two types of mid-foot amputation: Lisfranc amputation and Chopart amputation. In Lisfranc amputation, the fore-foot is amputated at the tarsometatarsal joints, with the lateral three metatarsals being separated from the cuboid and lateral cuneiform and the first and second metatarsals being separated from the medial and intermediate cuneiform respectively. In Chopart amputation, the fore-foot is removed at the midtarsal joint and a disarticulation occurs through the talonavicular and calcaneocubiod joints. In each case, the amputee retains the anile joint and its associated flexibility.

Although Chopart/Lisfranc amputees retain a significant portion of their anatomical ankle and heel, and thus may still partially rely on their anatomical ankle for motion, it is nonetheless desirable to provide a relatively lightweight and reliable prosthetic foot for Chopart/Lisfranc amputees that is capable of some of the motion, flexion, and cushion normally provided by the anatomical foot.

Some conventional prosthetic feet for Chopart/Lisfranc amputees employ a rigid, relatively flat prosthetic keel that is glued to the bottom of a socket worn by the amputee. In such conventional prostheses for Chopart/Lisfranc amputees, the resulting butt joint may be relatively weak since it relies solely upon the glue to hold it together. To increase the strength of such a butt joint, the surface area of the butt joint may be increased. For example, in some conventional foot prostheses for Chopart/Lisfranc amputees, the socket may be attached along up to 50% of the length of the keel. However, such a relatively large, rigid connection may detrimentally reduce the flexibility of the prosthetic foot as well as increase the bulk of the prosthetic foot, making it more difficult to wear and fit into a standard shoe or sneaker.

Thus, there remains a need to develop methods and apparatus for improved prostheses for Chopart/Lisfranc amputees which overcome some of the foregoing difficulties while providing more advantageous overall results.

BRIEF SUMMARY OF SOME OF THE PREFERRED EMBODIMENTS

These and other needs in the art are addressed in one embodiment by a prosthetic foot for attachment to a socket worn by an amputee. In an embodiment, the prosthetic foot comprises a body including a forefoot portion and a heel portion. In addition, the prosthetic foot comprises at least one attachment member extending from the body and conformable to the socket.

These and other needs in the art are addressed in another embodiment by a prosthetic foot assembly. In an embodiment, the prosthetic foot assembly comprises a keel body having a top surface, a bottom surface, a toe end and a heel end, wherein the keel body has a length measured from the toe end to the heel end. In addition, the prosthetic foot assembly comprises a socket attached to the top side of the keel and adapted to receive a limb of an amputee, wherein the socket contacts no more than 35% of the length of the keel as measured from the heel end.

These and other needs in the art are addressed in another embodiment by a method for assembling a prosthetic foot. In an embodiment, the method comprises providing a keel body having a top surface and a bottom surface and at least one attachment member extending from the body. In addition, the method comprises providing a socket adapted to receive a limb of an amputee and having a bottom surface and a side surface. Further, the method comprises attaching the socket bottom surface to the top surface of the keel body. Still further, the method comprises conforming and affixing the at least one attachment member to the socket side surface.

The foregoing has outlined rather broadly the features and technical advantages of embodiments of the present invention in order that the detailed description that follows may be better understood. Additional features and advantages of embodiments of the invention will be described hereinafter. It should be appreciated by those skilled in the art that the conception and the specific embodiments disclosed herein may be readily utilized as a basis for modifying or designing other structures for carrying out the same purposes of embodiments described herein. It should also be realized by those skilled in the art that such equivalent constructions do not depart from the scope of the invention as set forth in the appended claims.

BRIEF DESCRIPTION OF THE DRAWINGS

For a more detailed description of the preferred embodiment of the present invention, reference will now be made to the accompanying drawings, wherein:

FIG. 4 is a cross-sectional side view of the keel of FIG. 1;

FIG. 5 is an enlarged schematic cross-sectional side view of an embodiment of the forefoot portion of the keel illustrated in FIG. 4;

DETAILED DESCRIPTION OF THE INVENTION

Figure 1:
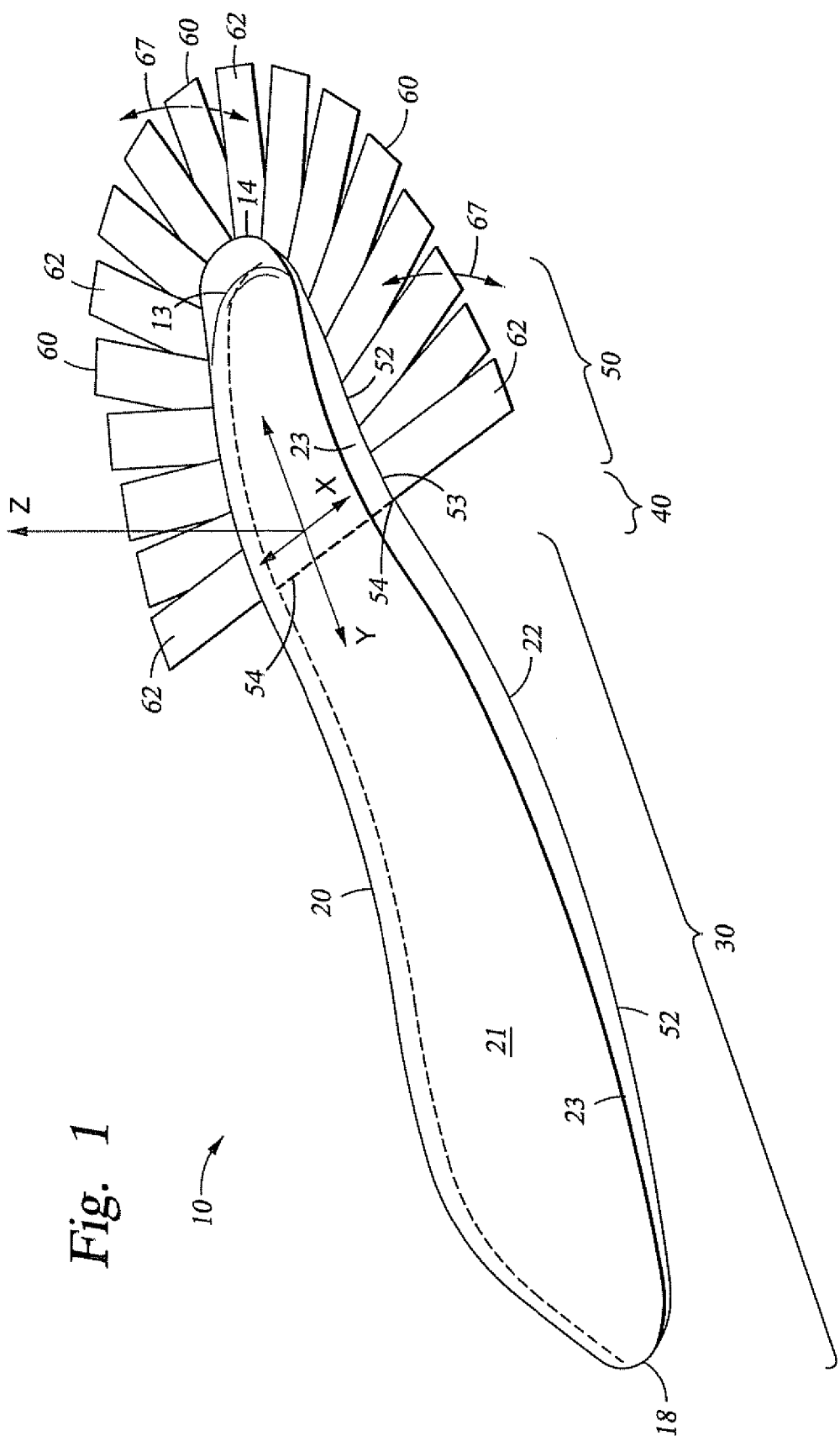
FIG. 1 is a perspective view of an embodiment of a prosthetic foot keel.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular system components. As one skilled in the art will appreciate, different persons may refer to a component by different names. This document does not intend to distinguish between components that differ in name but not function. The drawing figures are not necessarily to scale. Certain features of the invention may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the terms "connect," "attach," "couple" and the like are all intended to encompass both indirect and direct connections, attachments, etc. Thus, if a first device is connected to a second device, that connection may be through a direct connection, or through an indirect connection via other devices and connections.

For purposes of discussion, composites, or composite materials, are materials consisting of more than one constituent material. Some composites are composed of at least two constituent materials, namely a matrix, which may be continuous and may surround a second phase termed a substrate (e.g., dispersed phase, reinforcing phase). The substrate may be embedded in the matrix. The substrate (e.g., dispersed phase, reinforcing phase) may comprise any suitable material including without limitation, a metal or metal alloy (e.g., aluminum, titanium, stainless steel, etc.), a non-metal (e.g., fiberglass, carbon fiber, kevlar, quartz, polymer, ceramic, etc.) or combinations thereof. In addition, the substrate may comprise more than one constituent material (e.g., a substrate may comprise both carbon fibers and glass fibers). Likewise, the matrix of a composite may comprise any suitable material including without limitation, a metal or metal alloy (ergo, aluminum, titanium, stainless steel, copper, etch), a non-metal (e.g., resin, epoxy, polyester, polymer, ceramic, urethane, elastomer, etc.), or combinations thereof.

For purposes of this discussion, the x-, y-, and z-axes are shown in FIG. 1 and have been assigned as follows. The x-axis is perpendicular to both the leg and foot, passing through the sides of the ankle. Generally, dorsiflexion and planiflexion (e.g., movement of the ball of the foot upward and downward, respectively) may occur about the x-axis. The y-axis is perpendicular to the leg and parallel to the foot. Generally, inversion and eversion (e.g., the twisting of the foot around its longitudinal axis) may occur about the y-axis. The z-axis is parallel to the leg. Generally, transverse rotation (rotation of the foot with respect to the longitudinal axis of the leg) may occur about the z-axis. It is to be understood that the three axes (x-axis, y-axis, and z-axis) are orthogonal. In addition, in the context of the present discussion, "length" refers to a distance substantially along the y-axis, "width" refers to a distance substantially along the x-axis, and "thickness" refers to a distance substantially along the z-axis.

FIG. 1 illustrates an embodiment of a prosthetic foot keel 10 comprising a keel body 20 and a plurality of attachment members 60. Keel body 20 has a top surface 21, a bottom surface 22, a toe end 18, and a heel end 14. Keel body 20 further includes a sidewall 23 extending around the entire outer perimeter of keel body 20 between top surface 21 and bottom surface 22. A lower edge 52 is formed at the intersection of bottom surface 22 and sidewall 23.

In addition, keel body 20 can be thought of as comprising a forefoot portion 30, an interface region 40, and a heel portion 50. Interface region 40 defines the general boundaries of forefoot portion 30 and heel portion 50 and also defines the general region at which forefoot portion 30 and heel portion 50 intersect. Forefoot portion 30 includes toe end 18 and is continuous with interface region 40 and heel portion 50. Heel portion 50 includes heel end 14, an upper concavity or recess 13 in top surface 21, a lower recess 53 in bottom surface 22, and is contiguous with interface region 40 and forefoot portion 30. The overall length of keel body 20 is the sum of the lengths of forefoot portion 30, interface region 40, and heel portion 50. In preferred embodiments, keel body 20 ranges in length from 22 to 30 cm. Further, in preferred embodiments, heel portion 50, as defined by the location of interface region 40, represents 20% to 35% of the length of keel body 20.

Figure 2:
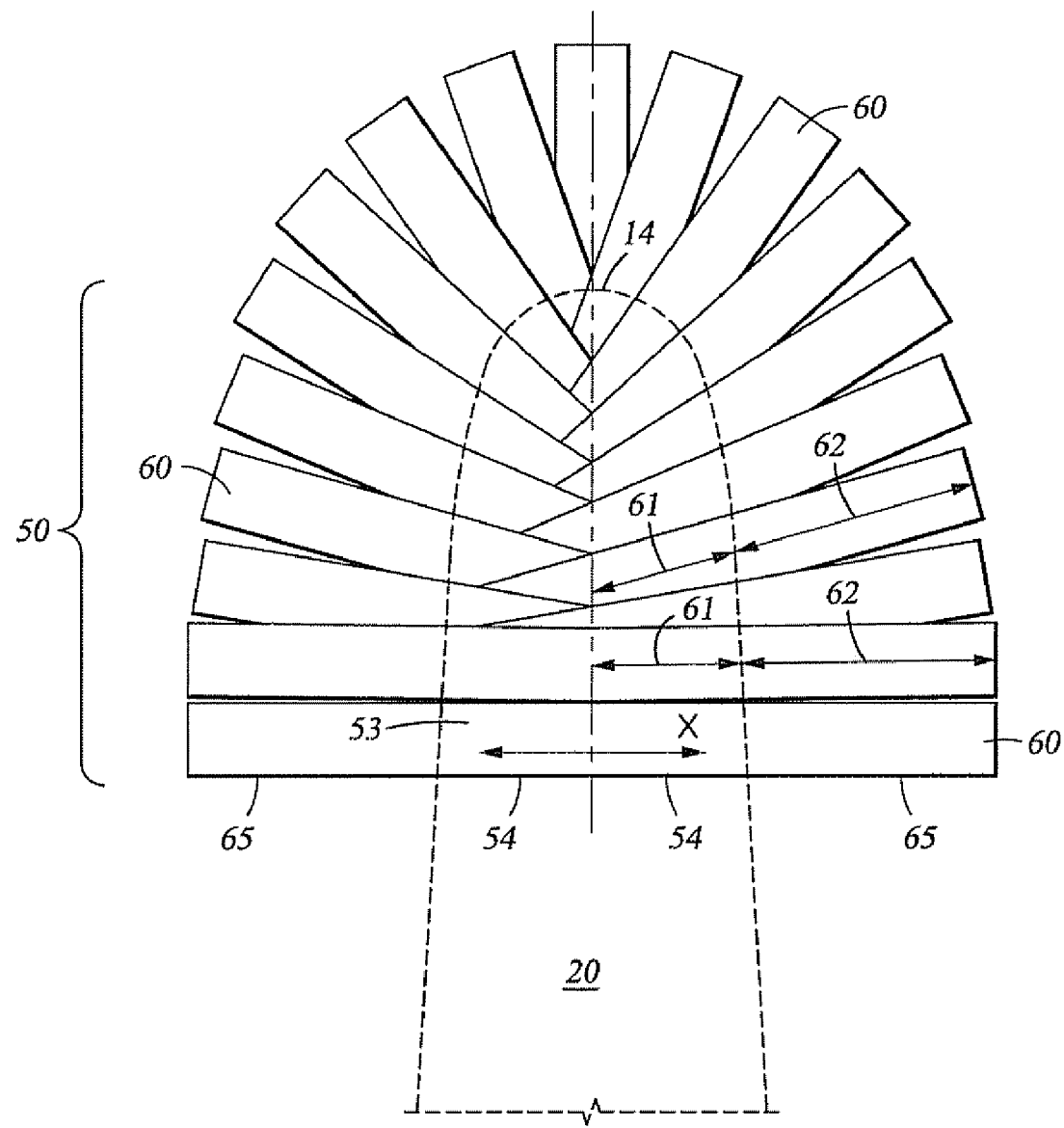
FIG. 2 is a bottom view of the heel portion of the keel of FIG. 1.

Referring to FIGS. 1 and 2, each elongated attachment member 60 includes a fixed section 61 and a free section 62 (best seen in FIG. 2). The fixed section 61 of each attachment member 60 is securely attached the bottom surface 22 of heel portion 50. In particular, the fixed section 61 of each attachment member is received in a recess 53 provided in the bottom surface 22 of heel portion 50.

Each free section 62 extends radially from lower edge 52 of heel portion 50. In this embodiment, free sections 62 extend from heel portion 50 along the entire lower edge 52 of heel portion 50 (e.g., free sections 62 extend from all portions of lower edge 52 of heel portion 50 from recess termination 54 to heel end 14). In different embodiments (not illustrated), free sections 62 may only extend from particular portions of lower edge 52 of heel portion 50.

The fixed section 61 of each attachment member 60 is preferably securely fixed to heel portion 50 such that each attachment member 60 does not move relative to heel portion 50. However, although each attachment member 60 is fixed to heel portion 50, each free section 62 extending from heel portion 50 may flex generally about lower edge 52 in the general direction(s) represented by arrows 67, generally towards the positive z-axis (above top surface 21) or negative z-axis (below bottom surface 22). Attachment members 60 may be attached to keel body 20 by any suitable means including without limitation, adhesive (e.g., glue, epoxy resin, etch), screws, bolts, or combinations thereof, or may be formed integrally with keel body 20.

As previously discussed, attachment members 60 are disposed within recess 53 in bottom surface 22 of heel portion 50. Lower recess 53 begins at a recess termination 54 substantially proximal interface region 40, and extends to heel end 14. In certain embodiments, recess termination 54 (shown in phantom in FIG. 1) is a recessed ridge that runs completely across keel body 20 generally in the direction of the x-axis (best seen in FIG. 2). Recess termination 54 may serve as a guideline to position attachment members 60 during manufacturing, and may also serve to maintain the position of attachment members 60 by limiting shifting of attachment member 60 relative to heel portion 50. For instance, a straight side 65 of some attachment members 60 may butt up against recess termination 54 and thereby be prevented from shifting of such attachment members towards toe end 18.

Attachment members 60 illustrated in FIG. 2 are shown as attached to heel portion 50 in a partially woven configuration in which some attachment members 60 overlap adjacent attachment members 60. However, in general, one or more attachment members 60 may be configured in any suitable manner including without limitation, an intermeshed weave, a non-intermeshed weave, an overlapping weave, a configuration in which no two attachment members 60 contact each other, or combinations thereof.

In the embodiments illustrated in FIGS. 1 and 2, attachment members 60 are disposed within recess 53 and attached to bottom surface 22 of heel portion 50. However, in other embodiments (not illustrated), attachment members 60 may be coupled to bottom surface 22 of heel portion 50, top surface 21 of heel portion 50, be integral with heel portion 50, or combinations thereof. Further, in the embodiments illustrated in FIGS. 1 and 2, a plurality of attachment members 60 extend from heel portion 50. However, in some embodiments, one or more attachment members 60 may extend from heel portion 50, interface region 40, forefoot region 30, or combinations thereof. Further, although each attachment member 60 illustrated herein is an elongated rectangular strip of material, in general, each attachment member 60 may comprise any suitable geometry.

Figure 3:
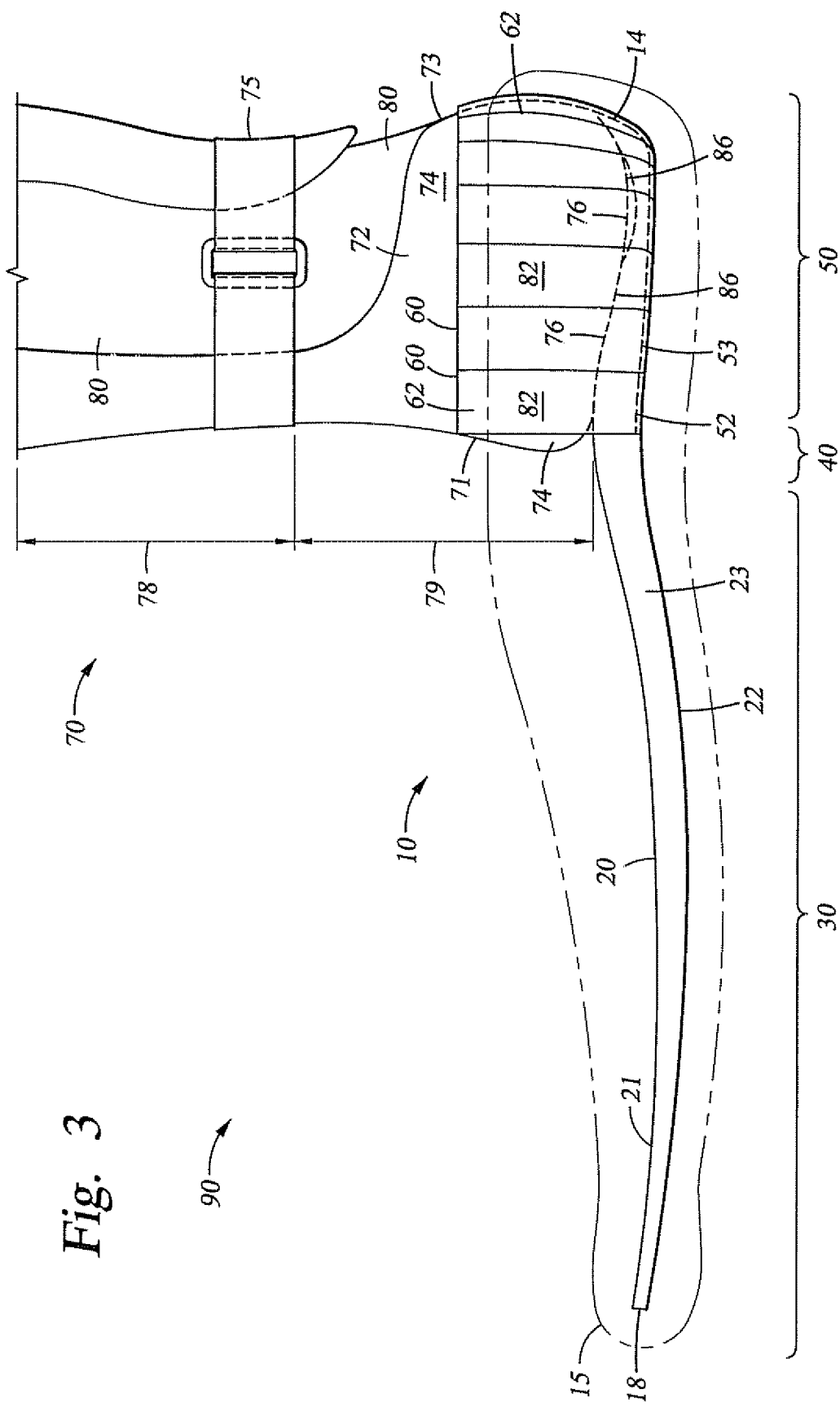
FIG. 3 is a side view of an embodiment of a prosthetic foot assembly including the keel of FIG. 1 coupled to a socket.

As best seen in FIG. 3, attachment members 60 are employed to securely and reliably attach prosthetic foot keel 10 and keel body 20 to a socket 70 worn by an amputee, thereby creating a prosthetic foot assembly 90.

FIG. 3 illustrates an embodiment of a prosthetic foot assembly 90. Prosthetic foot assembly 90 comprises a prosthetic foot keel 10, including keel body 20 and attachment members 60, coupled to a socket 70. Socket 70 is a device used to secure the lower limb of an amputee to prosthetic foot assembly 90. A variety of socket(s) 70 for attaching a prosthesis to an amputee are known in the art. Typically, the amputee will place his/her limb in an optional soft liner 80 and then place the limb and liner 80 into socket 70, which is attached to a prosthetic foot keel 10. Finally, the amputee usually secures prosthetic foot assembly 90 to the limb and liner 80 by tightening socket 70 about the limb and liner 80 by a securing means such as a strap 75. Any liner and/or socket may be used with embodiments of prosthetic foot assembly 90 described herein.

Socket 70 typically comprises an upper portion 78 and a lower portion 79. Lower portion 79 is below upper portion 78 relative to the z-axis. Upper portion 78 may be secured around the lower calf of a Chopart/Lisfranc amputee. The remaining heel and ankle of a Chopart/Lisfranc amputee may be positioned within lower portion 79.

Lower portion 79 includes an outer surface 74. Outer surface 74 generally comprises an outer front surface 71, an outer rear surface 73, an outer bottom surface 76, and two outer lateral surfaces 72 on either side of socket 70.

Prosthetic foot keel 10 is directly attached to socket 70 by a butt joint 86 and a plurality of lap joints 82. Top surface 21 of heel portion 50 is firmly fixed to outer bottom surface 76 of socket 70 to form butt joint 86 therebetween. As used herein, the term "butt joint" is used to describe a mechanical connection formed by two abutting surfaces. Outer bottom surface 76 of socket 70 may be attached to top surface 21 of heel portion 50 by any suitable means including, without limitation, adhesives (e.g., glue, epoxy resin, etc.), screws, bolts, or combinations thereof. In embodiments in which heel portion 50 is a composite material such as a carbon and glass fiber substrate and epoxy matrix composite, top surface 21 of heel portion 50 may be fixed to bottom surface 76 of socket 70 by epoxy resin.

The direct connection between socket 70 and prosthetic foot keel 10 is further secured, strengthened, and reinforced by lap joints 82. In particular, each free section 62 of each attachment member 60 is directly attached to outer surface 74 of lower portion 79 of socket 70 to form a plurality of lap joints 82. To reduce the potential for detrimental cutting and/or abrasion of attachment member 60 at lower edge 52, in select embodiments, lower edge 52 can be smoothly beveled or radiused. As used herein, the term "lap joint(s)" is used to describe a mechanical connection formed by overlapping and fastening together surfaces of two different components so as to produce a substantially flush and/or continuous surface.

In the embodiment illustrated in FIG. 3, free sections 62 are directly attached to both outer lateral surfaces 72 and rear surface 73 of lower portion 79 of socket 70. In other embodiments, lap joints 82 may be formed between prosthetic foot keel 10 and socket 70 at any suitable location including without limitation, outer front surface 71, one or more outer lateral surfaces 72, rear surface 73, upper portion 78, or combinations thereof.

Preferably, one or more attachment members 60 comprise a relatively lightweight, relatively strong, and relatively flexible material. Attachment members 60 are preferably strong to reduce the likelihood of premature breaking and/or failure of the connection of prosthetic foot keel 10 to socket 70. Premature failure or damage to the connection (e.g., cracking) may lead to injury of the amputee and/or repair/replacement expenses. Attachment members 60 are preferably relatively flexible so that attachment members 60 can be bent around lower edge 52 of heel portion 50 and conformed to the general shape of outer surface 74 of socket 70 when attached to outer surface 74 of socket 70, thereby increasing the surface area and strength of each lap joint 82. In select embodiments, attachment members 60 comprise a carbon and glass fiber material that is fixed to socket 70 by an epoxy resin. In such embodiments, the flexible glass and carbon fiber attachment members are formed into a relatively rigid carbon and glass fiber substrate and epoxy matrix composite when securely attached to outer surface 74 of socket 70 with an epoxy resin.

Some conventional prosthetic foot assemblies for Chopart/Lisfranc amputees employ a conventional socket, the bottom surface of which is glued to the top surface of a prosthetic foot keel to form a butt joint. Such a butt joint alone may be relatively weak since it may rely exclusively upon the glue to hold it together. In such conventional Chopart/Lisfranc assemblies, the strength of such a butt joint may be improved by increasing the contact surface area of the butt joint (e.g., glue more length of keel to the socket). For example, in some conventional prosthetic foot assemblies for Chopart/Lisfranc amputees, the butt joint may cover up to 50% of the length of the keel. However, since the butt joint tends to be very rigid, increasing the length and surface area of the butt joint may detrimentally reduce the flexibility of the prosthetic foot. Further, increasing the area of the butt joint may increase the overall bulk of the prosthetic foot, making it more difficult to wear and fit into a standard shoe or sneaker. Moreover, a socket and butt joint attached to about 50% of a keel may not have the same visual appearance as a natural anatomical foot.

Referring again to FIG. 3, embodiments of the present invention employ a butt joint 86 and a plurality of reinforcing lap joints 82 to provide additional strength and reliability to the connection between prosthetic foot keel 10 and socket 70. Further, by employing lap joints 82, embodiments described herein may reduce the length and surface area of butt joint 86 (e.g., reduce the length of the keel portion that is attached to socket 70), without compromising strength and reliability of the connection. In particular, in some embodiments, heel portion 50 and butt joint 86 represents no more than 35% of the length of keel body 20 from heel end 14. In select embodiments, heel portion 50 and butt joint 86 comprise 20% to 30% of the length of keel body 20 from heel end 14. By reducing the length of the rigid attachment between keel body 20 and socket 70, embodiments of prosthetic foot keel 10 may be relatively flexible as compared to some conventional prosthetic foot assemblies for Chopart/Lisfranc amputees. Further, by reducing the length of attachment between keel body 20 and socket 70, embodiments of prosthetic foot assembly 90 may be less bulky, and better simulate the appearance of an anatomical foot.

FIG. 3 also shows a cosmesis 15 (shown in phantom) that substantially surrounds keel body 20 and provides the external appearance of prosthetic foot keel 10. In select embodiments, cosmesis 15 is constructed of foamed polyethylene and ethylene-vinyl acetate copolymer (EVA). Further, in certain embodiments, the inside of cosmesis is formed of expanded polyethylene and the outside is formed of expanded EVA, which provides superior abrasion resistance.

FIG. 4 illustrates a cross section of keel body 20 shown in FIGS. 1 and 3. For purposes of clarity, attachment member 60 is excluded from this view. Forefoot portion 30 and heel portion 50 intersect at interface region 40. In the embodiment illustrated in FIG. 4, interface region 40 is located between 15% and 35% of the length of keel body 20 from heel end 14. Preferably, interface region 40 is located between 20% and 30% of the length of keel body 20 from heel end 14. Thus, referring to FIGS. 1-4, heel portion 50, lower recess 53, and butt joint 86 preferably substantially represent between 20% and 30% of the length of keel body 20 from heel end 14.

Referring specifically to FIG. 4, bottom surface 22 of forefoot portion 30 is slightly convex and includes a roll contact point 17 positioned along the length of forefoot portion 30. Roll contact point 17 may be in the general region about which forefoot portion 30 of prosthetic foot keel 10 contacts the ground during a normal forward or backward step. The generally smooth convex shape of bottom surface 22 forward and rearward of contact point 17 may desirably enhance the smoothness and ease of walking for an amputee. In select embodiments, roll contact point 17 may be located between 30% and 50% of the length of keel body 20, from toe end 18. Preferably, roll contact 17 is located between 35% and 45% of length of keel body 20, from the toe end 18.

Still referring to FIG. 4, top surface 21 of forefoot portion 30 is slightly concave. Further, in this embodiment, the thickness of forefoot portion 30 varies along the length of forefoot portion 30. In particular, the thickness of forefoot portion 30 increases from toe end 18 to interface region 40. In other words, forefoot portion 30 tapers (e.g., becomes thinner) from interface region 40 to toe end 18. The taper of forefoot portion 30 may be linear or non-linear. Due to the taper of forefoot portion 30, concave top surface 21 of forefoot portion 30 and convex bottom surface 22 of forefoot portion 30 are not exactly parallel. In over embodiments (not illustrated), forefoot portion 30 may be of uniform thickness (e.g., forefoot portion 30 does not taper), in which case top surface 21 of forefoot portion 30 and bottom surface 22 of forefoot portion 30 may be substantially parallel.

in general, the thickness of forefoot portion 30 and any taper of forefoot portion 30 may be a function of numerous factors including without limitation, the length of forefoot portion 30, the length of keel body 20, the intended use of prosthetic foot keel 10 (e.g., geriatric amputee, athletic amputee, etc.), the amount of desired flexion in keel body 20, the desired weight of prosthetic foot keel 10, the forces applied to keel body 20, or combinations thereof.

Heel portion 50 includes a generally concave upper recess 13 in top surface 21 of heel portion 50 and lower recess 53 in the bottom surface of heel portion 50. As best seen in FIG. 3, heel portion 50 supports a significant amount of the load imparted by the amputee (e.g., amputee's weight). Top surface 21 of heel portion 50, including upper recess 13, is a smoothly curved surface capable of distributing such applied forces. Without being limited by theory, by distributing forces, a relatively smooth top surface 21 may reduce or minimize stress concentrations which may otherwise result in premature damage or cracking of keel body 20.

In addition, as best seen in FIG. 3, heel portion 50 is attached to socket 70 which is worn by an amputee. The smooth concave geometry of top surface 21 of heel portion 50 permits for a variety of orientations of prosthetic foot keel 10 relative to socket 70 when keel 10 is initially fixed to socket 70. In particular, the smooth concave geometry of top surface 21 of heel portion 50 permits the adjustment of keel body 20 about the x-axis, the y-axis, and the z-axis, relative to socket 70 during assembly of prosthetic foot assembly 90.

Referring again to FIG. 4, inclusion of upper recess 13 in heel portion 50 results in the thickness of heel portion 50 increasing from heel end 14 towards interface region 40. In other words, heel portion 50 tapers from interface region 40 to heel end 14 (e.g., heel portion 50 gets thinner towards heel end 14). As previously discussed, lower recess 53 accommodates one or more attachment members 60 in bottom surface 22 of heel portion 50. Lower recess 53 permits attachment of attachment member 60 to heel portion 50 without significantly increasing the thickness of heel portion 50.

In addition, tapering of heel portion 50 may reduce the weight of heel portion 50. Moreover, by reducing the thickness of heel portion 50 via tapering, additional padding can be accommodated between top surface 21 of heel portion 50 and the amputee's limb without resulting in an unduly bulky prosthesis. Such additional padding may increase the cushion of prosthetic foot keel 10 and thereby improve the comfort of prosthetic foot keel 10. In contrast, the heel portion of some conventional prosthetic foot assemblies may be made relatively thick for strength purposes, especially near regions likely to sustain flexion. In such a conventional prosthetic foot assembly, additional padding between the heel portion and the amputee's limb may excessively increase the bulk of the prosthesis. Such a prosthetic may not visually replicate an anatomical foot because it appears artificially large or thick. Further, a relatively thick heel portion plus additional padding may render the prosthesis too heavy for some patients (e.g., geriatric patients).

Referring again to FIG. 4, forefoot portion 30 is contiguous with interface region 40, and interface region 40 is contiguous with heel portion 50, however, each portion of keel body 20 (e.g., forefoot portion 30, interface region 40, heel portion 50, etc,) may comprise a different material. In the embodiment illustrated in FIG. 4, forefoot portion 30 comprises a first material 31, while heel portion 50 and interface region 40 comprise a second material 51. In different embodiments, interface region 40 may comprise the same material as forefoot portion 30, heel portion 50, or a third different material. Further, in select embodiments (not illustrated), each portion of keel body 20 may comprise the same material (e.g., first material 31 and second material 51 may be the same material).

First material 31 may comprise any suitable material(s) including without limitation metals and metal alloys (e.g., stainless steel, aluminum, titanium, etc.), non-metals (e.g., composite, polymer, elastomer, ceramic, etc.), or combinations thereof. Further, first material 31 may comprise more than one constituent material (e.g., laminate of different materials, composite, etc,). First material 31 preferably comprises a relatively lightweight, relatively rigid material capable of withstanding repeated application of forces (e.g., forces applied at roll contact 17 during walking). Further, first material 31 preferably comprises a material capable of some flexion, provides some cushion, and has the ability to return to its original unflexed position following removal of forces from forefoot portion 30.

Referring to FIG. 5, an embodiment of forefoot portion 30 and first material 31 is illustrated. In this embodiment, first material 31 comprises a top layer 32, a middle layer 34, and a bottom layer 36. In other embodiments, first material 31 may comprise one or more constituent material(s).

Middle layer 34 is positioned between top layer 32 and bottom layer 36. Middle layer 34 may be held in place by any suitable means including without limitation, adhesive, pressure, friction, screws, or combinations thereof. For example, middle layer 34 may be held in place by pressure acting at the interface of middle layer 34 and top layer 32 and pressure acting at the interface of middle layer 34 and bottom layer 36. For instance, top layer 32 and bottom layer 36 may comprise relatively rigid materials that act as springs exerting force on middle layer 34 when middle layer 34 is inserted between top layer 32 and bottom layer 36 and tends to push apart top layer 32 and bottom layer 36. In select embodiments, middle layer 34 extends from toe end 18 to proximal interface region 40 between forefoot portion 30 and heel portion 50.

In select embodiments, top layer 32 and bottom layer 36 each comprise a relatively lightweight and rigid composite (e.g., glass fiber substrate and epoxy matrix composite, carbon fiber substrate and epoxy matrix composite, carbon and glass fiber substrate and epoxy matrix composite, etc.) and middle layer 34 comprises a more flexible elastomer or polymer (e.g., neoprene, polyethylene, cellulose acetate, polypropylene, etc.). In this configuration, top layer 32 and bottom layer 36 may provide a spring effect, while middle layer 34 may provide a cushion effect. The spring effect may provide a means to absorb, store, and release energy, thereby allowing keel body 20 to return to a relaxed, unflexed position when applied forces are removed. Achievement of a spring effect without additional hardware (e.g., coil springs or other reciprocating means that absorb, store and release energy) may desirably reduce the weight of keel body 20. Further, the use of composite materials in top layer 32 and bottom layer 36 may reduce the weight of keel body 20 while providing some rigidity and strength.

Still further, this configuration may allow for some flexibility along the length of forefoot portion 30. The amount of flexion permitted by forefoot portion 30 relative to interface region 40 is preferably at least 5°. For example, a carbon and glass fiber substrate mid epoxy matrix composite top layer 32 and bottom layer 36 may permit 10° of flexion (dorsiflexion and/or planiflexion) of forefoot portion 30 relative to interface region 40 when keel body 20 is fixed to an amputee. Depending on the overall length of forefoot portion 30, such flexion may permit toe end 18 to flex over half an inch relative to interface region 40. This flexion capability of forefoot portion 30 may advantageously simulate the flexion and cushion normally provided by an anatomical foot. However, ultimately, the desired amount of flexion of forefoot portion 30 may be a function of numerous factors including without limitation, the personal preferences of the amputee, the activity level of the amputee, the weight of the amputee, whether amputee is geriatric, or combinations thereof.

Referring again to FIG. 4, heel portion 50 and interface region 40 comprise second material 51. Second material 51 may comprise one or more constituent material(s). Second material 51 may comprise any suitable material(s) including without limitation metals mid metal alloys (e.g., stainless steel, aluminum, titanium, etc ), non-metals (e.g., composite, polymer, elastomer, ceramic, etc.), or combinations thereof. Further, second material 51 may comprise more than one constituent material (e.g., laminate of different materials, composite, etc.).

Second material 51 is preferably capable of providing a firm base for attachment of socket 70 to heel portion 50 (see FIG. 2). As best seen in FIG. 3, heel portion 50 is desirably firmly and securely coupled to a socket 70 worn by an amputee. To enhance the strength and reliability of the connection between keel body 20 and socket 70, second material 51 preferably comprises a rigid material that is securely fixed to socket 70 such that keel body 20 does not move rotationally or translationally relative to socket 70. Thus, second material 51 may be a relatively stiff material with very limited flexibility. Further, second material 51 is preferably strong enough to withstanding repeated application of forces (e.g., forces applied to heel portion 50, heel end 14, etc.) and capable of withstanding stress concentrations and slight bending which may occur as forefoot portion 30 flexes relative to heel portion 50. Although strength and rigidity are desirable, second material 51 is also preferably lightweight to minimize the bulk and weight of prosthetic foot keel 10. In some embodiments, second material 51 comprises a glass fiber substrate and epoxy matrix composite. In other embodiments, second material 51 comprises a carbon fiber substrate and epoxy matrix composite. Preferably, second material 51 comprises a carbon and glass fiber substrate and epoxy matrix composite. In this configuration, heel portion 50 is relatively strong, rigid and lightweight.

Figure 6:
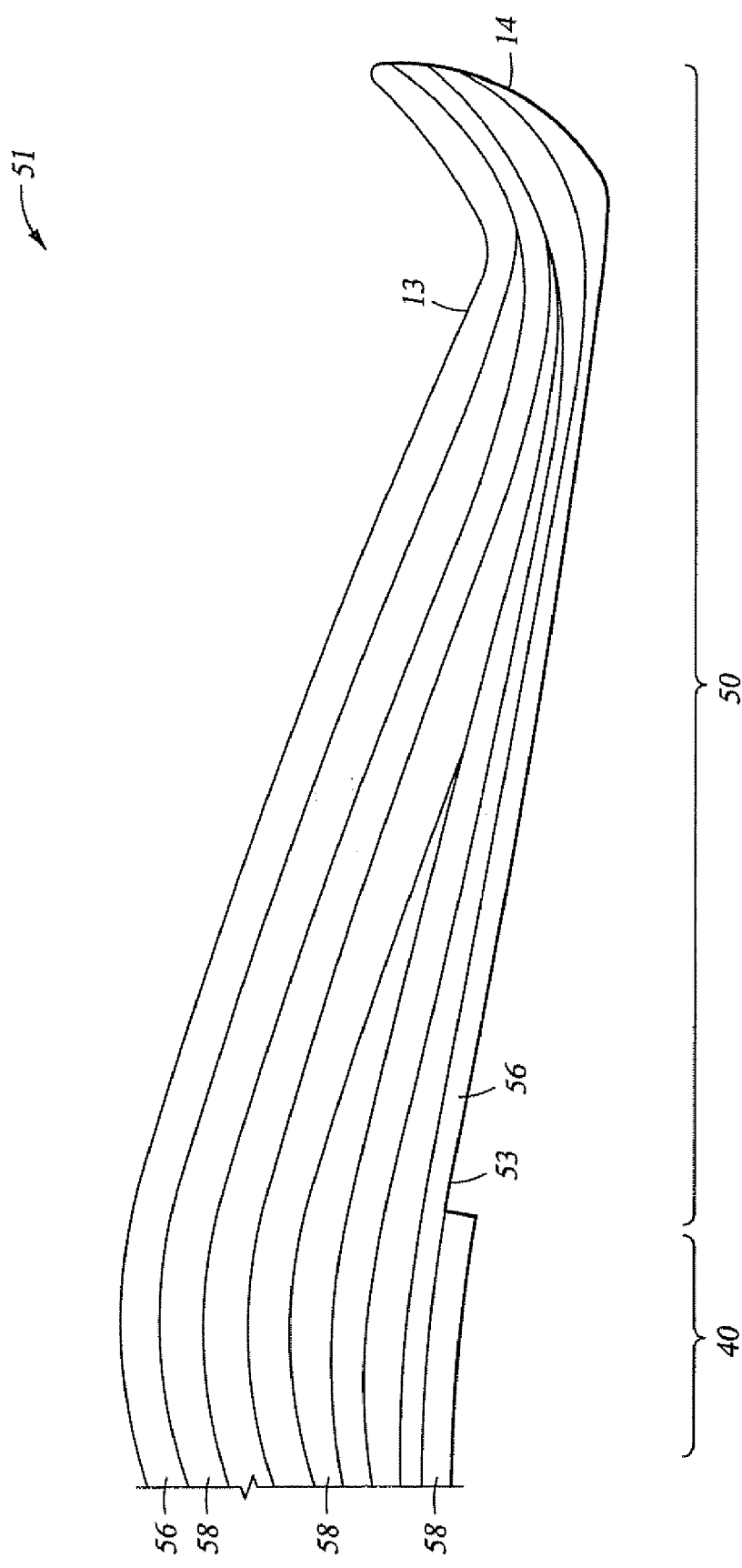
FIG. 6 is an enlarged schematic cross-sectional side view of an embodiment of the heel portion of the keel illustrated in FIG. 4.

Referring to FIG. 6, an embodiment of heel portion 50, interface region 40, and second material 51 is illustrated. In this embodiment, second material 51 comprise a fiber composite (e.g., glass fiber substrate and epoxy matrix composite, carbon fiber substrate and epoxy matrix composite, carbon and glass fiber substrate and epoxy matrix, etc,). Interface region 40 is formed by a plurality of fibers 56, 58 which pass through interface region 40 into heel portion 50. Heel portion 50 is formed by a plurality of short fibers 58 and a plurality of long fibers 56. Short fibers 58 extend from forefoot portion 30 across interface region 40 into heel portion 50, but do not fully extend to heel end 14. Long fibers 56 extend from forefoot portion 40 through interface region 40 to heel end 14. In this manner, by reducing the total number of fibers along the length of heel portion 50 from mid-foot portion 40 to heel end 14, the effective thickness of heel portion 50 is reduced. Further, by selectively choosing the locations at which short fibers 58 terminate along the length of heel portion 50, upper recess 13 and lower recess 53 may be formed as part of heel portion 50. In certain embodiments, long fibers 56 (e.g., fibers that extend from mid-foot portion 40 through heel end 14) represent 20% to 30% of the substrate fiber in heel portion 50 sunning along the longitudinal axis of keel body 20, while short fibers 58 (e.g., fibers that do not extend completely to heel end 14) represent 70% to 80% of the substrate fibers in heel portion 50 running alone the longitudinal axis of keel body 20.

Referring again to FIG. 4, as previously described, forefoot portion 30 and heel portion 50 are thickest proximal interface region 40. Consequently, interface region 40 is the thickest portion of keel body 20. Interface region 40 is desirably the thickest portion of keel body 20 to maximize the strength of keel body 20 at interface region 40. In particular, as previously described, once heel portion 50 is securely and firmly fixed to socket 70 (as best seen in FIG. 3), heel portion 50 and attachment members 60 are relatively rigid and stiff. However, as previously described, forefoot portion 30 preferably provides some flexion and cushion to simulate an anatomical foots. Thus, in some embodiments, interface region 40 lies at the intersection of a relatively stiff, rigid heel portion 50 and a relatively flexible forefoot portion 30. As a result, as forefoot portion 30 flexes relative to heel portion 50, keel body 20 will have a tendency to bend at interface region 40 and areas proximal interface region 40. Such focused bending within keel body 20 may lead to stress concentrations potentially resulting in premature cracking, breaking, or damage to keel body 20. However, by providing a relatively thick interface region 40, the strength of interface region 40 may be increased, thereby reducing the potential for undesirable cracking, breaking, and damage at interface region 40.

Referring still to FIG. 4, keel body 20 is preferably constructed of relatively lightweight and strong composite materials, As discussed above, each portion of keel body 20 may comprise a different composite material. Preferably, first material 31 (forefoot portion 30) and second material 51 (heel portion 50 and interface region 40) each comprise a composite material that share a common substrate that extends through the forefoot, the mid-foot, and the heel. For example, first material 31 may comprise a carbon and glass fiber composite and second material 51 may comprise a carbon and glass fiber composite. In this configuration, some carbon and glass fibers (substrate) may continuously extend through first material 31, through interface region 40, and through second material 51. This arrangement may result in a contiguous, unitary, and relatively strong keel body 20. However, by varying the matrix within each portion of keel body 20, and/or by adding additional constituents to each portion of keel body 20 (e.g., adding a neoprene middle layer 34 in forefoot portion 30), different portion of keel body 20 may have distinct mechanical characteristics. In this manner, each portion of keel body 20 may be custom designed to provide different characteristics. For example, forefoot 30 may provide a spring effect, cushion, and some flexion; the relatively thick regions proximal interface region 40 may provide a rigid, strong, relatively inflexible portion adapted to withstand flexion; and heel portion 50 may provide a relatively lightweight, strong and rigid material.

In general, the thickness of each portion of keel body 20 (e.g., forefoot portion 30, interface region 40, and heel portion 50) will tend to be a fiction of numerous factors including without limitation, the length of keel body 20, the intended use of keel body 20 and prosthetic foot keel 10 (e.g., geriatric amputee, athletic amputee, etc.), the amount of flexion desired in keel body 20, the desired weight of keel body 20 and prosthetic foot keel 10, the forces applied to keel body 20, location of high stress regions, or combinations thereof.

Figure 7:
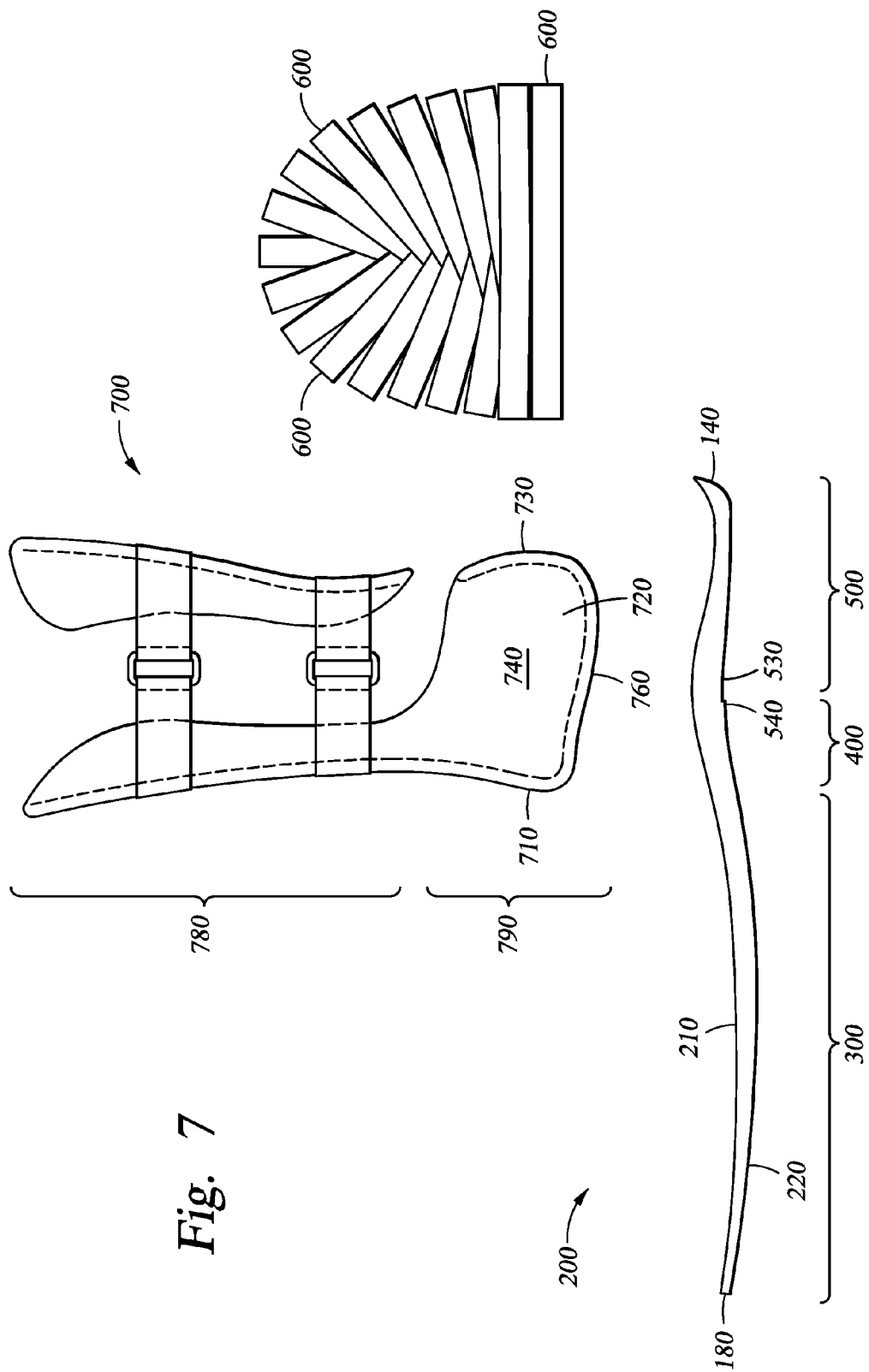
FIGS. 7-9 are sequential views showing assembly of an embodiment of a prosthetic foot assembly.
Figure 8:
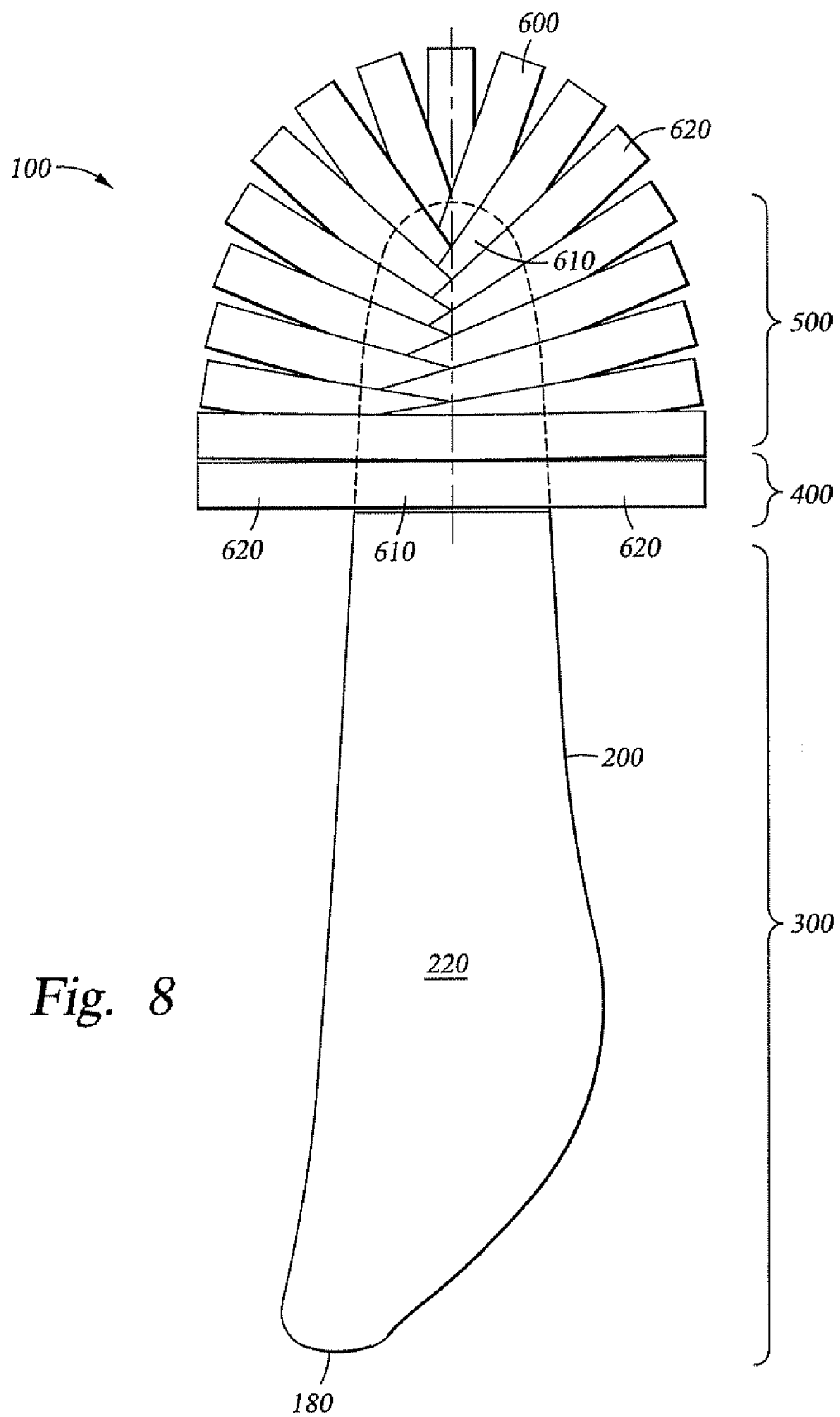
Figure 9:
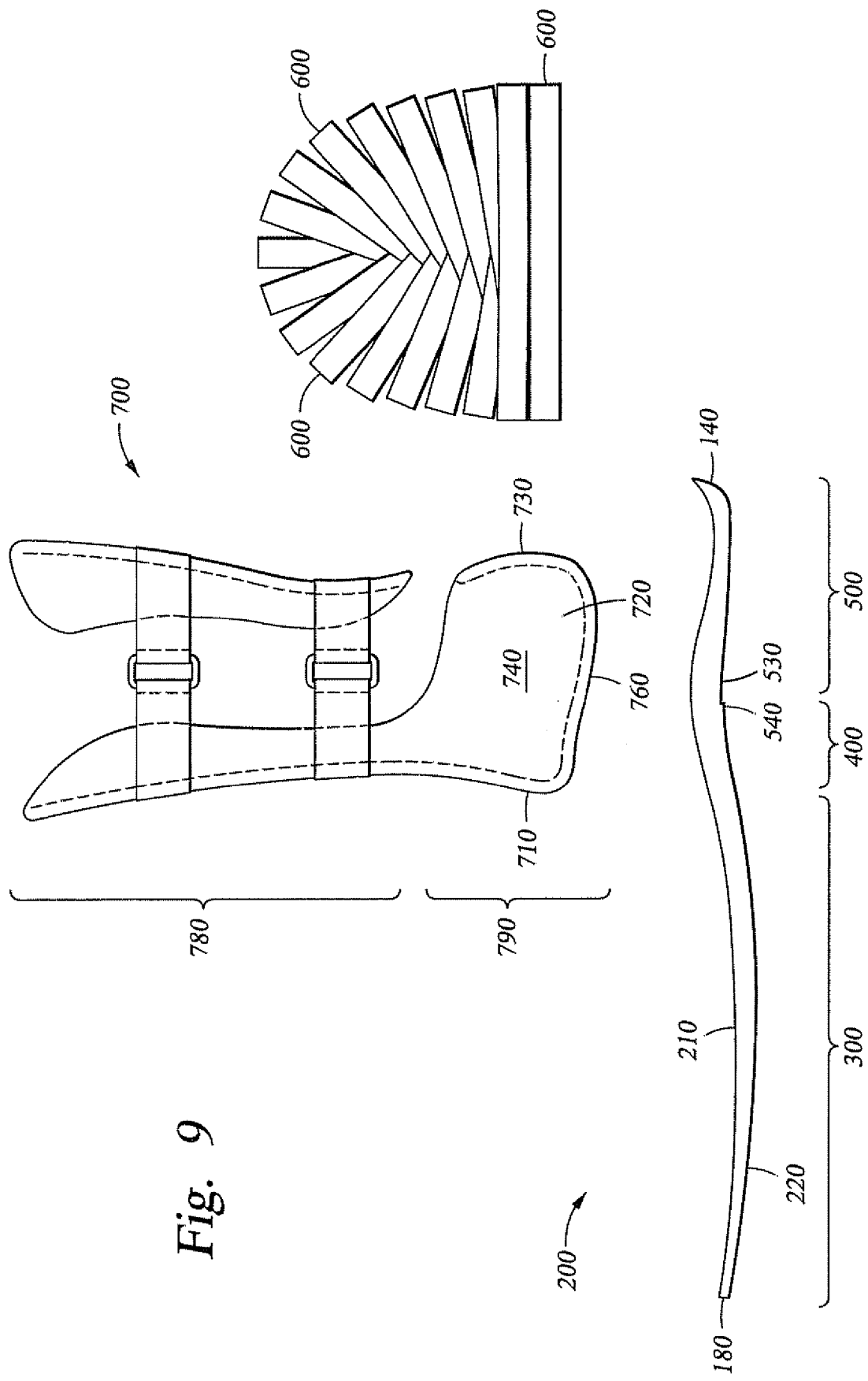

FIGS. 7-9 illustrate sequential views of the formation of a prosthetic foot assembly 900. Prosthetic foot assembly 900 is worn on the lower limb of a Chopart/Lisfranc amputee who has suffered a forefoot disarticulation, but has retained a heel and at least a portion of an ankle. Such an amputee may partially rely on his/her remaining ankle to provide motion and flexion.

Referring to FIG. 7, the basic components used to create prosthetic foot assembly 900 include a keel body 200, a plurality of attachment members 600, and a socket 700. Socket 700 is worn by the amputee may comprise any conventional socket or frame. Socket 700 comprises an upper portion 780 and a lower portion 790. Lower portion 790 includes an outer surface 740. In some embodiments, lower portion 790 includes an outer bottom surface 760, an outer front surface 710, an outer rear surface 730, and two outer lateral surfaces 720.

Keel body 200 simulates the anatomical foot and includes a forefoot portion 300, a heel portion 500, and an interface region at the intersection of forefoot portion 300 and heel portion 500. A lower recess 530 is provided in the bottom surface 220 of heel portion 500. Lower recess 530 begins at a recess termination 540 and extends to a heel end 140. Recess termination 540 runs across the width of keel body 200 proximal interface region 400 Keel body 200 may be similar to embodiments of keel body 20 illustrated in FIGS. 1-4.

Each attachment member 600 comprises a generally elongated rectangular shape. However, in general, each attachment member may have any suitable shape including without limitation rectangular, circular, triangular, semi-circular, etc. The plurality of attachment members 600 are formed generally in a fanned/semicircular arrangement. Attachment members 620 may be attached to each other or not attached to each other.

As best seen in FIG. 8, the plurality of attachment members 600 are attached to bottom surface 220 of heel portion 500 thereby forming a prosthetic foot keel 100. In particular, attachment members 600 are positioned within lower recess 530. Recess termination 540 may be used to align attachment members 600 and further, may be used to prevent shifting of attachment members 600 towards toe end 180 during assembly. Attachment member 600 may be fixed to keel body 200 by any suitable manner. In select embodiments in which heel portion 500 comprises a carbon and glass fiber substrate and epoxy matrix composite and attachment member 600 comprises a carbon and/or glass fiber material, attachment members 600 may be securely fixed within lower recess 530 by apply an epoxy resin that is allowed to dry, thereby forming a rigid, secure connection between attachment member 600 and heel portion 500. Once attached to heel portion 500, each attachment member has an attached section 610 fixed to bottom surface 220 of heel portion 500 and a free section 620 that extends from heel portion 500.

As best seen in FIG. 9, once attachment members 600 are securely and firmly attached to heel portion 500, socket 700 may be attached to prosthetic foot keel 100, thereby forming a prosthetic foot assembly 900. To attach prosthetic foot keel 100 to socket 700, bottom surface 760 of socket 700 is directly attached to top surface 210 of heel portion 500, thereby forming a butt joint 860. Bottom surface 760 may be attached to heel portion 500 by any suitable manner. In select embodiments in which heel portion 500 comprises a carbon and glass fiber substrate and epoxy matrix composite, bottom surface 760 may be adhered to top surface 210 of heel portion 500 with an epoxy resin.

Once bottom surface 760 is securely and firmly attached to top surface 210 of heel portion 500, each attachment member 600 is curved upwards toward outer surface 740 of socket 700 and positioned in contact with outer surface 740 of socket 700. In particular, some attachment members 600 are positioned in contact with outer lateral surfaces 720, and some attachment members are positioned in contact with outer rear surface 730 of socket 700. Then each attachment member 600 is fixed to outer surface 740, thereby forming a plurality of lap joints 820 between each free section 820 and outer surface 740, In general, attachment member 600 may be fixed to side surfaces 720 and rear surface 730 of socket 700 by any suitable means. In select embodiments in which attachment member 600 and lapping members 610 comprise a carbon and/or glass fiber material, attachment member 600 may be securely fixed to side surfaces 720 and rear surface 730 of socket 700 by apply an epoxy resin that is allowed to dry, thereby forming a rigid, secure connection between attachment member 600 and socket 700.

Butt joint 820 between top surface 210 of heel portion 500 and bottom surface 760 of socket 700 and lap joints 820 between attachment members 600 and outer surface 740 of socket 700 work together to provide a rigid, secure, and reliable connection between prosthetic foot keel 100 and socket 700. Such a rigid, secure, and reliable connection has the potential to reduce premature breaking of the connection between prosthetic foot keel 100 and socket 700. Further, such a rigid, secure, and reliable connection has the potential to reduce the bulk and improve the flexibility of keel body 200 by reducing the length of keel body 200 that may be required if a butt joint alone is used to secure keel body 200 to socket 700.

While the embodiments shown in FIGS. 7-9 illustrate an embodiment of the invention in which attachment members 600 are provided as separate components that are attached to the underside of keel 100, it will be understood that other methods for constructing the present assembly are also possible. For instance, attachment members could be formed integrally with keel 100. In this embodiment, fibers for forming attachment members 600 might be emplaced in a mold along with the fiber component of the keel and the matrix component of the keel might be molded such that fibers for forming attachment members 600 extended from the finished keel. Attachment members 600 might comprise only fibers, which are subsequently impregnated with a polymer or other adhesive during attachment to socket 700. Alternatively, attachment members 600 could be impregnated with an resilient matrix prior to being attached to socket 700.

In the manner described, embodiments of the present invention provide certain mechanical improvements over the prior art. Some embodiments of the present invention have the advantage of providing a relatively lightweight prosthetic foot assembly capable of partially simulating the flexion normally provided by an anatomical foot. In particular, embodiments of the present invention provide for a dynamic response prosthetic foot assembly for Chopart/Lisfranc amputees designed to provide sufficient flexion to partially simulate the flexion normally provided by the anatomical foot. In addition, embodiments of the present invention have the advantage of providing a strong, rigid, and secure means of coupling a prosthetic foot keel to a socket worn by an amputee. In particular, embodiments of the prosthetic foot assembly described herein include both a butt joint and one or more lap joints between the prosthetic foot keel and the socket.

Several useful discussions of the context and usage of prosthetic feet are given in U.S. Pat. Nos. 5,482,513, 5,443,527, 5,116,384, which are all hereby incorporated by reference herein in their entireties. For example, the construction of a suitable cosmesis, prosthetic leg attachment, and composition of various components can be derived from those disclosures.

While preferred embodiments of this invention have been shown and described, modifications thereof can be made by one skilled in the art without departing from the scope or teaching of this invention. The embodiments described herein are exemplary only and are not limiting. Many variations and modifications of the system and apparatus are possible and are within the scope of the invention. For example, the relative dimensions of various parts, the materials from which the various parts are made, and other parameters can be varied, so long as the embodiments retain the advantages discussed herein. For instance, while the embodiments described above are preferably constructed of fiber composites because of its lightness, strength, flexibility and resiliency, it will be understood that other materials may be equally suitable. Accordingly, the scope of protection is not limited to the embodiments described herein, but is only limited by the claims that follow, the scope of which shall include all equivalents of the subject matter of the claims.

What is claimed is:

1. A prosthetic foot for attachment to a socket worn by an amputee, comprising:
    a keel body extending along a central axis from a toe end to a heel end, wherein the keel body includes a top surface extending from the toe end to the heel end and a bottom surface extending from the toe end to the heel end, the top surface facing upwards and the bottom surface facing downwards;
    wherein the keel body has a length measured along the central axis from the toe end to the heel end;
    wherein the keel body includes a forefoot portion, a heel portion, and an interface region at the intersection of the forefoot portion and the heel portion;
    wherein the heel portion extends from the heel end to the interface region and the forefoot portion extends from the toe end to the interface region;
    wherein the bottom surface includes a recess in the heel portion, the recess extending axially from the interface region to the heel end;
    at least one attachment member extending from said keel body and conformable to the socket;
    wherein each attachment member includes a fixed section and a free section, wherein the fixed section of each attachment member is completely disposed within the recess and is directly attached to the bottom surface of the keel body in the heel portion, and the free section of each attachment member extends radially from the heel portion.

2. The prosthetic foot according to claim 1 wherein said attachment member is formed integrally with the keel body.

3. The prosthetic foot of claim 1, wherein the top surface of the keel body in the heel portion includes a concave recess.

4. The prosthetic foot of claim 1, wherein the interface region is located between 20% and 30% of the length from the heel end.

5. The prosthetic foot of claim 4, wherein the forefoot portion has a forefoot thickness that increases from the toe end to the interface region.

6. The prosthetic foot of claim 4, wherein the heel portion has a heel thickness that increases from the heel end to the interface region.

7. The prosthetic foot of claim 1, wherein the forefoot portion comprises a first material and the heel portion comprises a second material and wherein the first and second materials are different.

8. The prosthetic foot of claim 7, wherein the second material comprises a glass and carbon fiber substrate and epoxy matrix composite.

9. The prosthetic foot of claim 1, wherein each attachment member comprises a flexible fiber.

10. The prosthetic foot of claim 1, wherein each attachment member comprises glass and carbon fibers and is affixed to the socket with an epoxy resin.

11. A prosthetic foot assembly, comprising:
 a keel body extending along a central axis from a toe end to a heel end, wherein the keel body has a top surface extending from the toe end to the heel end and a bottom surface extending from the toe end to the heel end, the top surface facing upwards and the bottom surface facing downwards;
 wherein the keel body includes a forefoot portion including a toe end, and a heel portion including a heel end, and wherein the keel body has a length measured along the central axis from the toe end to the heel end;
 a plurality of attachment members, wherein each attachment member has a fixed section engaging the bottom surface of the keel body in the heel portion and a free end extending from the heel portion of the keel body; and
 a socket adapted to receive a limb of an amputee, wherein the socket is oriented perpendicular to the keel body and includes an upper portion and a lower portion, the upper portion adapted to be disposed about the calf of the amputee and the lower portion adapted to be disposed about the heel or ankle of the amputee;
 wherein the lower portion of the socket includes an outer front surface facing in the direction of the toe end, an outer rear surface facing in the direction of the heel end, an outer bottom surface facing downward, and a pair of outer lateral surfaces, wherein each outer lateral surface extends between the outer front surface and the outer rear surface, and the outer bottom surface extends between the outer front surface, the outer rear surface, and the outer lateral surfaces;
 wherein the outer bottom surface of the lower portion of the socket engages and is directly attached to the top surface of the keel body in the heel portion with a butt joint, wherein butt joint has a length measured along the central axis from the heel end that is no more than 35% of the length of the keel body; and
 wherein the free end of at least one of the attachment members engages and is directly attached to one of the outer lateral surfaces of the lower portion of the socket or the outer rear surface of the lower portion of the socket with a lap joint.

12. The assembly of claim 11, wherein the fixed end of each attachment member is directly attached to the heel portion of the keel body and the free end of each attachment member is directly attached to the socket.

13. The assembly of claim 12, wherein the free end of each attachment member engages and is directly attached to the one of the outer lateral surfaces of the lower portion of the socket or the outer rear surface of the lower portion of the socket with a lap joint.

14. The assembly of claim 11, wherein the length of the butt joint is no more than 30% of the length of the keel body.

15. The assembly of claim 11, wherein at least a portion of the keel body comprises a glass and carbon fiber substrate and epoxy matrix composite.

16. The assembly of claim 11 wherein each of said attachment members comprises glass and carbon fibers.

17. A method for assembling a prosthetic foot, comprising:
 a) providing a keel body, wherein the keel body extends along a central axis from a toe end to a heel end, and wherein the keel body has a top surface facing upwards, a bottom surface facing downwards, and at least one attachment member having a fixed end connected to the keel body and a free end extending from said keel body;
 b) providing a socket adapted to receive a limb of an amputee, wherein the socket is oriented perpendicular to the keel body and includes an upper portion and a lower portion, the upper portion adapted to be disposed about the calf of the amputee and the lower portion adapted to be disposed about the heel or ankle of the amputee, and wherein the lower portion of the socket includes an outer bottom surface facing downward and a pair of outer lateral surfaces, wherein the outer bottom surface extends between the outer lateral surfaces;
 c) engaging the top surface of the keel body with the outer bottom surface of the lower portion of the socket;
 d) attaching the outer bottom surface of the lower portion of the socket to the top surface of the keel body;
 e) rotating the free end of the at least one attachment member upward and into engagement with one of the outer lateral surfaces of the socket; and
 f) affixing the free end of the at least one attachment member to the side surface of the socket.

18. The method of claim 17 wherein the socket contacts no more than 30% of the length of the keel body as measured from a heel end of the keel body.

* * * * *